United States Patent
Nielsen et al.

(10) Patent No.: US 9,827,347 B2
(45) Date of Patent: Nov. 28, 2017

(54) PRESSURE SENSITIVE ADHESIVE COMPOSITION

(75) Inventors: Anders Christian Nielsen, Bagsvaerd (DK); Tune Bjarke Bonné, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 246 days.

(21) Appl. No.: 14/237,169

(22) PCT Filed: Aug. 9, 2012

(86) PCT No.: PCT/DK2012/000091
§ 371 (c)(1),
(2), (4) Date: Feb. 5, 2014

(87) PCT Pub. No.: WO2013/020556
PCT Pub. Date: Feb. 14, 2013

(65) Prior Publication Data
US 2014/0213955 A1  Jul. 31, 2014

(30) Foreign Application Priority Data
Aug. 9, 2011 (DK) .................................. 2011 70437

(51) Int. Cl.
*A61L 24/04* (2006.01)
*C09J 153/02* (2006.01)
*A61L 15/58* (2006.01)
*C09J 7/02* (2006.01)

(52) U.S. Cl.
CPC ........... *A61L 24/043* (2013.01); *A61L 15/585* (2013.01); *C09J 7/0221* (2013.01); *C09J 153/02* (2013.01); *A61L 2400/14* (2013.01); *C09J 2409/00* (2013.01); *C09J 2425/00* (2013.01); *C09J 2453/00* (2013.01)

(58) Field of Classification Search
CPC .... A61L 15/585; A61L 2400/14; C08L 1/286; C08L 53/02; C09J 7/0221; C09J 153/02; C09J 2425/00; C09J 2453/00
See application file for complete search history.

(56) References Cited

U.S. PATENT DOCUMENTS

| | | |
|---|---|---|
| 3,339,546 A | 9/1967 | Chen |
| 4,231,369 A | 11/1980 | Sorensen |
| 4,367,732 A | 1/1983 | Poulsen |
| 5,369,155 A | 11/1994 | Asmus |
| 6,803,400 B1 | 10/2004 | Butterbach |
| 7,285,576 B2 | 10/2007 | Hyde |
| 7,321,007 B2 | 1/2008 | Gagliardi |
| 2005/0123590 A1 | 6/2005 | Burton |
| 2005/0163978 A1 | 7/2005 | Strobech |
| 2007/0078448 A1* | 4/2007 | Lipman ............... A61L 15/58 606/9 |
| 2010/0233273 A1 | 9/2010 | Burton |
| 2011/0150993 A1* | 6/2011 | Zhang ............. A61K 9/2059 424/464 |

FOREIGN PATENT DOCUMENTS

| | | |
|---|---|---|
| EP | 1762206 A1 | 3/2007 |
| WO | 9817212 A1 | 4/1998 |
| WO | 9954422 | 10/1999 |
| WO | 2007093186 A1 | 8/2007 |
| WO | 2007128320 A2 | 11/2007 |
| WO | 2008154928 | 12/2008 |
| WO | 2009006900 | 1/2009 |
| WO | 2009006902 | 1/2009 |
| WO | 2009102933 A1 | 8/2009 |
| WO | 2010069333 | 6/2010 |
| WO | 2010069334 A1 | 6/2010 |

OTHER PUBLICATIONS

Arkon P-115, Product data sheet, May 2000.
Arkon P-140, Product data sheet, May 2000.

* cited by examiner

*Primary Examiner* — Suzanne Ziska
*Assistant Examiner* — Thurman Wheeler
(74) *Attorney, Agent, or Firm* — Coloplast Corp., Coloplast A/S; Nick Baumann

(57) ABSTRACT

A pressure sensitive adhesive composition includes 4-15 w/w % styrene-isoprene-styrene copolymer, 20-35 w/w % styrene-isoprene diblock copolymer, 4-15 w/w % tackifier, 6-18 w/w % paraffin oil, and 30-45 w/w % hydrocolloid. The size of the hydrocolloid is below 40 μm.

10 Claims, No Drawings

PRESSURE SENSITIVE ADHESIVE COMPOSITION

FIELD OF THE INVENTION

The present invention relates to a pressure sensitive adhesive composition for attachment to human skin and medical devices including such composition.

BACKGROUND

For a long time, pressure sensitive adhesives have been used for attaching medical devices, such as ostomy appliances, dressings (including wound dressings), wound drainage bandages, devices for collecting urine, orthoses and prostheses to the skin.

Hydrocolloid adhesives containing hydrophilic particles or absorbents, which absorb moisture into the adhesive bulk and transmit moisture when conditions are saturated, are one well-known group of pressure sensitive adhesives useful for attaching medical devices to the skin. However, the retention of moisture in hydrocolloid adhesives may cause changes in the adhesive, such as swelling, loss of cohesion and disintegration. Non-absorbing adhesives on the other hand, may trap excessive moisture between the skin and adhesive, causing weakening of adhesion and maceration of the skin.

When hydrocolloid particles are incorporated into adhesives, the properties of the resulting adhesives change. Typically, the hardness of the adhesive will increase with the addition of hydrocolloid. This is often undesired in medical devices as it is preferred to have soft and skin-friendly adhesives being capable of following the movements of the skin. Furthermore, it is a disadvantage that the processing of the adhesive will be more difficult when working with hydrocolloid containing adhesives. Due to the increased hardness of the adhesive, the tackiness of the adhesive matrix decrease and may, prior to addition of hydrocolloids, need to be increased by increasing the adhesiveness of the composition, enhancing the risk of damaging the skin when the device is removed.

Due to the delicate nature of skin, there is a narrow window where a pressure sensitive adhesive can function as a good and skin friendly adhesive: On one hand, the adhesive should be able to attach the medical device to the skin and the device should not fall off during wear and, on the other hand, removal of the medical device from the skin should not cause damage to the skin.

It has now surprisingly been found that a pressure sensitive adhesive composition can be made that is useful in medical devices, which can be removed without pain. Furthermore, the adhesive composition of the invention maintain the absorbing characteristic, while being applied in a thin layer.

SUMMARY OF THE INVENTION

The present invention relates to a pressure sensitive adhesive composition comprising 4-15 w/w % SIS (styrene-isoprene-styrene copolymer),
20-35 w/w % SI (styrene-isoprene) diblock copolymer,
4-15 w/w % tackifier,
6-18 w/w % paraffin oil, and
30-45 w/w % hydrocolloid, wherein the size of the hydrocolloid is below 40 µm.

DETAILED DESCRIPTION OF THE PRESENT INVENTION

The aim of the invention is to provide a pressure sensitive adhesive composition that can be used on a thin wound dressing, which can be removed without pain and at the same time keep the ability to absorb moisture despite the thin construction of the medical device.

The pressure sensitive adhesive composition according to the invention can also be used beneficially in thicker constructions.

The pressure sensitive adhesive composition according to the invention may be used on a wound dressing suitable for coldsore and small scratches, especially on the face. The application of the adhesive may be suitable for elderly skin, kids, and post operational areas.

The continuous phase of the pressure sensitive adhesive composition according to the invention is based on the mixture of A-B-A block copolymers with A-B block copolymers.

The pressure sensitive adhesive composition according to the invention comprises 4-15 w/w % SIS (styrene-isoprene-styrene copolymer).

Furthermore, the sensitive adhesive composition according to the invention comprises 20-35 w/w % SI (styrene-isoprene) diblock copolymer.

The styrene-isoprene block copolymer may increase the peel and tack, however, without increasing the hardness of the adhesive.

According to one embodiment of the invention, the styrene-isoprene block copolymer has a molecular weight of 34000-45000 g/mol.

The pressure sensitive adhesive composition according to the invention comprises 4-15 w/w % tackifier. The tackifier may be a hydrocarbon resin or a low molecular weight thermoplastic hydrocarbon resin or a mixture thereof. The tackifier introduces tack to the adhesive.

In one embodiment of the invention, the adhesive composition comprises a tackifying resin such as natural, modified or synthetic resins, preferably polar resins such as rosins, rosin esters, hydrogenated rosins, hydrogenated rosin esters, and derivatives of such polar resins or pure aromatic monomer resins.

Tackifying resins can be added to control tack in the adhesives, i.e. reduce moduli and increase glass transition temperature.

Moreover, the pressure sensitive adhesive composition according to the invention comprises 6-18 w/w % paraffin oil such as mineral oil. The paraffin oil adjusts the hardness and the tack of the adhesive.

Oils that can support good water vapour permeability are preferred. Examples of such oils are liquid rosin derivates, aromatic olefin oligomers as well as vegetable and animal oils and derivatives thereof.

The discontinuous phase of the pressure sensitive adhesive composition according to the invention includes hydrocolloid with a certain size.

The pressure sensitive adhesive composition according to the invention comprises 30-45 w/w % hydrocolloid, wherein the size of the hydrocolloid is below 40 µm, preferably below 20 µm.

In one embodiment of the invention, D50 is below 30 µm. By D50 is meant that 50 v/v % of the hydrocolloids are below 30 µm in size.

Suitable hydrocolloids for incorporation in the adhesive compositions of the invention are selected from naturally occurring hydrocolloids, semi-synthetic hydrocolloids and synthetic hydrocolloids. Varieties of hydrocolloids within the scope of the present invention include synthetic polymers prepared from single or multiple monomers, naturally occurring hydrophilic polymers or chemically modified naturally occurring hydrophilic polymers. The hydrocolloid polymers may be linear or cross-linked.

More particularly, the hydrocolloids are preferably selected from guar gum, locust bean gum (LBG), pectin, alginates, gelatine, xanthan and/or gum karaya; cellulose derivatives (e.g. salts of carboxymethylcellulose such as sodium carboxymethylcellulose, methylcellulose and hydroxypropylmethylcellulose) and/or sodium starch glycolate and/or polyvinylalcohol and/or polyethylene glycol, polyhydroxyalkyl acrylates and methacrylates, polyacrylamides, polyacrylic acid, polystyrene sulfonates, natural or synthetically modified polysaccarides, such may be alginates, pectins, xantan gums, guar gum, chitosan, carboxy methyl cellulose and hydroxy ethyl or hydroxypropyl cellulose.

In an embodiment of the invention, the hydrocolloid is NaCMC (sodium carboxymethyl cellulose).

The hydrocolloid provides water handling to the adhesive, either through permeability or absorption capacity or both.

When a hydrocolloid containing adhesive is used in medical devices, such as wound dressings or ostomy appliances, the hydrocolloids will also serve as moisture transport from the skin or a wound through to the top the device. In order to optimise the moisture transporting properties of the device, a very permeable backing layer is normally used. However, a limiting factor in the moisture transport is often related to the interface between the film and the hydrocolloid particles of the adhesive. To achieve an adhesive with moisture transporting properties, an amount of at least 25% w/w hydrocolloids is needed.

The pressure sensitive adhesive composition according to the invention comprising small size hydrocolloids provides superior initial absorption, which is desired, e.g. in order to get good and fast adhesion to wet or moist surfaces.

The size of the hydrocolloid particles may be a limiting factor on the thickness of adhesive coatings. Very thin coatings may be desired in order to achieve a more flexible product as well as the breathability of the product may be enhanced.

Major moisture transmission improvements are obtained by addition of small size hydrocolloids to the adhesive matrix and it is possible to prepare very thin transmitting coatings of adhesive.

Apart from the actual weight gain, the cohesion of the swelled adhesive is important in order to render it possible to remove the adhesive without leaving residues.

The smaller size of the hydrocolloids in the adhesive composition of the invention may influence the rheological properties of the pressure sensitive adhesive composition of the invention. The viscosity and processing temperature will be lower than when using traditionally sized hydrocolloids, rendering it possible to prepare thinner coatings, e.g. adhesives with a thickness of less than 50 µm, and bevelling of the edge of a thick adhesive as well as the adhesive as such may be easier to mould.

According to an embodiment of the invention, the thickness of the adhesive is 30-40 µm.

The pressure sensitive adhesive composition according to the invention can be handled in a similar manner as the conventional hydrocolloid pressure sensitive adhesive system, however still maintaining the characteristics of flexibility, softness and the ability to absorb moisture.

When applying the adhesive in a simple application process without split release liners and paper frame, the initial adhesion or tack is another parameter of importance. The tack has to be sufficient to enable the product to adhere to the user's body upon application, but the tack should also be low enough to allow the user to re-applicate and adjust the product, if positioned incorrectly.

The pressure sensitive adhesive composition according to the invention fulfils this criterion.

If the tack of the adhesive is too weak, the adhesive cannot adhere properly to the skin. However, if the tack is too high, the adhesive will stick to the surface when trying to remove it, finally resulting in breaking the adhesive and leaving residues on the skin or causing skin stripping of the body. Neither option is desirable.

PSA adhesive types can be formulated into different tackiness. Tack depends of various factors like, type of substrate to be adhered on, aggressiveness, oil or resin content and type, rate of filling, chemistry etc.

General tack of state of the art PSA adhesives used in ostomy care is formulated to be relatively low, as a low tack is needed in order to be able to give a right position to the skin when a collecting device like an ostomy bag is applied to the abdomen. The tack desired should be sufficiently high for it to stay on the skin when applied, but will not bond to the skin at first skin contact. Adhesion to the skin will evolve with time and is accelerated if pressure is applied.

High tack adhesives that have acceptable peel force when removed from the skin do not have the feature of an easy application, as the high tack tends to bond to the skin at first skin contact.

The tack of the pressure sensitive adhesive composition according to the invention is similar to the tack of the conventional hydrocolloid pressure sensitive adhesive.

The peel force relates to the force applied to the adhesive for removing the adhesive from the skin. Suitably, the peel force applied at the removal does not cause pain for example by sticking to the hair of the skin.

A medical device according to the invention is typically in the form of a laminate comprising a backing layer, a layer of adhesive and which is optionally covered in part or fully by one or more release liners or cover films to be removed before use. The device may further comprise a secondary backing layer to be removed before use.

The adhesive composition may be placed on a backing layer.

According to an embodiment of the invention, a medical device comprises a backing layer and a layer of the pressure sensitive adhesive composition according to the invention.

The backing layer of the device according to the invention may be any layer, such as a polyurethane film, foam or non-woven or combination of films or layers which, in combination with the adhesive, shows the desired characteristics of the device according to the invention. The film may e.g. be produced from a polyolefinic material, PVAI, polyester, polyamide, silicones, Teflon®, polyurethane material or polyethylene or copolymers or blends thereof.

The film may be biodegradable or solubilised under certain conditions.

A preferred material for the backing layer may be polyurethane in the form of a film or a foam or combinations of such e.g. in the form of laminates.

The skin-contacting surface of the device may be covered by one or more release liners.

Release liners which are especially suitable for use with the device of the invention can be made of kraft papers, polyethylene, polypropylene, polyester or composites of any of these materials. The liners are preferably coated with release agents such as fluorochemicals or silicones. The release liner may, if present, be removed before, during or after application. If only removed after application, the release liner may act as a handle during application.

The adhesive layer may be in the form of a continuous layer or a pattern or the adhesive may only be situated on a part of the skin-facing side of the device, e.g. on a flange around the central part of the device to form an island dressing with a non-adhesive or low-adhesive absorbent pad at the central part of the dressing.

The medical device according to the invention may e.g. be a wound care device, continence device, breast care device, an ostomy appliance or any adhesive device for application to the skin.

According to an embodiment of the invention, the medical device is a dressing.

The medical device of the invention may be a dermatological dressing.

In one embodiment of the invention, the thickness of the dressing is 30-40 μm.

According to an embodiment of the invention, the medical device is an ostomy appliance.

EXPERIMENTAL

Ingredients

| | |
|---|---|
| Kraton D1163P | SIS (styrene-isoprene-styrene) copolymer |
| Kuraray LIR-310 | SI (styrene-isoprene) diblock copolymer |
| Arkon P90 | tackifier |
| Arkon P115 | tackifier |
| Arkon P140 | tackifier |
| Kristalex | tackifier |
| Paraffin oil | paraffin oil |
| Aquasorb A800 | hydrocolloid |

Preparation of the Adhesive

The adhesives were produced on a laboratory scale mixer, which could mix up to 500 g adhesive. The mixing was done in two steps, a premix and a finished mix.

The premix consisted of Kraton, LIR-310, Kristalex and paraffin oil, which was mixed at a temperature of 165° C. First, the Kraton was softened for approximately 20 minutes. Hereafter, the other ingredients were added and mixed until the mass had reached a temperature of 135° C., which could take up to two hours. Hereafter, the premix was removed from the mixer and cooled. The finished adhesive consisted of premix and Aquasorb, which was mixed at a temperature of 90° C. The premix and Aquasorb was mixed until the mass temperature reached 80° C., which was approximately 20 minutes. Finally, the mixture was cooled and the adhesive was ready.

Laboratory Methods

Method 1: Determination of Water Absorption

Absorption capacity was measured by mounting a 044 sample of adhesive on a small glass slide, submersing the adhesive in a 0.9% NaCl solution and measuring the weight gain as function of time. The water absorption was measured as $g/cm^2$.

Method 2: Peel

Peel adhesion was measured as 90° peel from steel plates, at 23° C., 50% RH, 304 mm/min, 25 mm broad samples, Instron model 5564 tensile tester (PSTC-2). The peel was measured as N/25 mm.

Method 3: Water Permeability

Moisture transmission was measured by an inverted Pattington cup method. The moisture vapour transmission was measured as $g/m^2/24$ hours in 0.9% NaCl, 37° C., 15% RH.

Method 4: Test of the Use of the Adhesive Composition 3 persons tested four different adhesive compositions.

The adhesives were placed on the arm of a person for 30 minutes.

At the removal, the person reported how painful it was to remove the adhesive from the skin and whether the adhesive was sticking to the hair of the arm.

A scale from 1-5 was used, wherein 1 means that the person feels no pain and 5 meaning that the removal is very painful.

| | 70-76 | 70-77 | 70-78 | 70-79 | 70-80 |
|---|---|---|---|---|---|
| Ingredients | | | | | |
| Kraton D1163P | 9.75 | 9.75 | 9.51 | 9.51 | 9.75 |
| Kuraray LIR-310 | 29.25 | 29.25 | 28.52 | 28.52 | 23 |
| Arkon P115 | | 7 | | | |
| Arkon P90 | | | 9.23 | | |
| Kristalex | | | | 9.23 | 10 |
| Arkon P140 | 13 | 6 | | | |
| Paraffin oil | 13 | 13 | 12.74 | 12.74 | 17.25 |
| Aquasorb A800 | 35 | 35 | 40 | 40 | 40 |
| Total | 100.00 | 100.00 | 100.00 | 100.00 | 100.00 |
| Water absorption Thickness 1 mm | | | | | |
| 30 min | 0.019 | 0.016 | 0.019 | 0.024 | 0.026 |
| 3 h | 0.020 | 0.017 | 0.051 | 0.098 | 0.072 |
| Peel Thickness 1 mm | | | | | |
| Mean (N/25 mm) | 19.62 | 20.18 | 11.79 | 10.49 | 8.63 |
| S:D | 0.59 | 1.08 | 0.45 | 0.45 | 1.51 |
| Water permeability Thickness 70-90 μm | | | | | |
| 24 h | | 593.65 | 849.14 | 554.28 | 514.18 |

-continued

|  | R1 | R2 | R3 | R4 | R5 | R6 | R7 | R8 |
|---|---|---|---|---|---|---|---|---|
| Ingredients |  |  |  |  |  |  |  |  |
| Kraton D1163P | 14.52 | 10.84 | 4.76 | 4.76 | 4.84 | 10.84 | 14.29 | 14.52 |
| Kuraray LIR-310 | 24.19 | 25.3 | 23.81 | 33.33 | 33.87 | 25.3 | 23.81 | 33.87 |
| Arkon P115 |  |  |  |  |  |  |  |  |
| Arkon P90 |  |  |  |  |  |  |  |  |
| Kristalex | 14.52 | 10.84 | 14.29 | 4.76 | 14.52 | 10.84 | 4.76 | 4.84 |
| Arkon P140 |  |  |  |  |  |  |  |  |
| Paraffin oil | 6.77 | 13.01 | 17.14 | 17.14 | 6.77 | 13.01 | 17.14 | 6.77 |
| Aquasorb A800 | 40 | 40 | 40 | 40 | 40 | 40 | 40 | 40 |
| Total | 100.00 | 99.99 | 100.00 | 99.99 | 100.00 | 99.99 | 100.00 | 100.00 |
| Water absorption Thickness 1 mm |  |  |  |  |  |  |  |  |
| 30 min | 0.080 | 0.049 | 0.041 | 0.040 | 0.062 | 0.058 | 0.047 | 0.071 |
| 3 h | 0.190 | 0.137 | 0.089 | 0.151 | 0.170 | 0.148 | 0.124 | 0.142 |
| Peel Thickness 1 mm |  |  |  |  |  |  |  |  |
| Mean (N/25 mm) | 12.36 | 11.68 | 11.7 | 17.19 | 21.89 | 10.86 | 11.08 | 15.35 |
| S:D | 0.82 | 0.89 | 1.12 | 2.05 | 1.15 | 0.27 | 0.29 | 1.85 |

Testing of removal

| R1 | R5 | R6 | R8 | 191 |
|---|---|---|---|---|
| 1.0 | 2.7 | 1.3 | 2.0 | 3.7 |

The adhesive composition 191 is used for comparing an adhesive composition known by the skilled person and refers to an adhesive composition comprising Kraton 1161 BT, Arkon P115, DOA, hydrocolloids and potato starch.

The invention claimed is:

1. A pressure sensitive adhesive composition comprising:
    4-15 w/w % of a SIS (styrene-isoprene-styrene copolymer),
    20-35 w/w % of a SI (styrene-isoprene) diblock copolymer,
    4-9.23 w/w % of a tackifier, wherein the tackifier is a hydrocarbon resin or a low molecular weight thermoplastic hydrocarbon resin or a mixture of a hydrocarbon resin and a low molecular weight thermoplastic hydrocarbon resin,
    6-18 w/w % of a paraffin oil, and
    30-45 w/w % of a hydrocolloid, wherein the size of the hydrocolloid is below 40 μm.

2. The pressure sensitive adhesive composition according to claim 1, wherein D50 of the size of the hydrocolloid is below 30 μm.

3. The pressure sensitive adhesive composition according to claim 1, wherein the size of the hydrocolloid is below 20 μm.

4. The pressure sensitive adhesive composition according to claim 1, wherein the hydrocolloid is NaCMC (sodium carboxymethyl cellulose).

5. The pressure sensitive adhesive composition according to claim 1, wherein the SI diblock copolymer has a molecular weight of 34,000-45,000 g/mol.

6. The pressure sensitive adhesive composition according to claim 1, wherein the paraffin oil is mineral oil.

7. A medical device comprising a backing layer and a layer of the pressure sensitive adhesive composition according to claim 1.

8. The medical device according to claim 7, wherein the medical device is a dressing.

9. The medical device according to claim 8, wherein a thickness of the dressing is 30-40 μm.

10. The medical device according to claim 7, wherein the medical device is an ostomy appliance.

* * * * *